United States Patent
Johnson

(10) Patent No.: US 10,502,237 B2
(45) Date of Patent: Dec. 10, 2019

(54) METHOD AND SYSTEM FOR ATTENUATING TRANSMISSION OF HIGH AMPLITUDE OSCILLATIONS BY A VACUUM SYSTEM

(71) Applicant: EDCO USA, Fenton, MO (US)

(72) Inventor: Edwin L. Johnson, Ballwin, MO (US)

(73) Assignee: EDCO USA, Fenton, MO (US)

( * ) Notice: Subject to any disclaimer, the term of this patent is extended or adjusted under 35 U.S.C. 154(b) by 116 days.

(21) Appl. No.: 13/663,011

(22) Filed: Oct. 29, 2012

(65) Prior Publication Data

US 2013/0108482 A1    May 2, 2013

Related U.S. Application Data

(60) Provisional application No. 61/552,306, filed on Oct. 27, 2011.

(51) Int. Cl.
| | |
|---|---|
| *F04F 5/20* | (2006.01) |
| *F16K 15/16* | (2006.01) |
| *A61M 1/00* | (2006.01) |
| *A61F 9/007* | (2006.01) |

(52) U.S. Cl.
CPC .............. *F04F 5/20* (2013.01); *A61M 1/0031* (2013.01); *F16K 15/16* (2013.01); *A61F 9/007* (2013.01); *A61M 1/0076* (2013.01); *A61M 2206/22* (2013.01); *A61M 2210/0612* (2013.01); *Y10T 137/0396* (2015.04)

(58) Field of Classification Search
CPC ....... F04F 5/00; F04F 5/44; F04F 5/20; F16K 15/16; A61M 1/0031; A61M 1/0076; A61M 2210/0612; A61M 2206/22; A61F 9/007; Y10T 137/0396
USPC .................... 417/190, 191; 137/513.3, 513.5
See application file for complete search history.

(56) References Cited

U.S. PATENT DOCUMENTS

| | | | | |
|---|---|---|---|---|
| 1,782,310 A | * | 11/1930 | Overstreet | F04F 5/461 417/172 |
| 3,454,182 A | * | 7/1969 | Morton | B61F 15/22 137/513.5 |
| 4,177,831 A | * | 12/1979 | Benjamin | F02M 1/14 137/513.5 |
| 4,649,984 A | * | 3/1987 | Bedell | B22D 11/0697 164/254 |
| 4,701,304 A | * | 10/1987 | Horn | B01J 19/0046 422/108 |
| 4,759,691 A | * | 7/1988 | Kroupa | F04F 5/467 417/174 |
| 4,869,290 A | * | 9/1989 | Sepso | F25B 41/06 137/513.3 |
| 4,880,358 A | * | 11/1989 | Lasto | F04F 5/22 417/174 |
| 5,126,712 A | * | 6/1992 | Sugiyama | F02N 15/00 277/636 |
| 5,228,839 A | * | 7/1993 | Peterson | F04F 5/22 417/174 |

(Continued)

*Primary Examiner* — Devon C Kramer
*Assistant Examiner* — Christopher J Brunjes
(74) *Attorney, Agent, or Firm* — Matthews Edwards LLC

(57) ABSTRACT

The method and system for attenuating or damping the amplitude of vacuum pressure oscillations in a vacuum system uses a flow-modulated damper to disperse and damp high-amplitude vacuum oscillations of a vacuum generator to a degree where fine vacuum control may be achieved for delicate work such as eye surgery.

13 Claims, 10 Drawing Sheets

(56) References Cited

U.S. PATENT DOCUMENTS

| | | | | |
|---|---|---|---|---|
| 5,456,287 | A | * | 10/1995 | Leu ................... F04B 39/1073 137/855 |
| 5,676,183 | A | * | 10/1997 | Bravo ................ B67D 7/0478 137/375 |
| 7,207,349 | B1 | * | 4/2007 | Yoshioka ................ F16K 17/30 137/513.5 |
| 8,485,220 | B2 | * | 7/2013 | Gutierrez ............. G05D 7/0133 137/513.3 |
| 2004/0182447 | A1 | * | 9/2004 | Nicolino ............... F16K 15/148 137/513.5 |
| 2005/0050855 | A1 | * | 3/2005 | Baptista ................ B65B 51/146 53/434 |
| 2006/0237185 | A1 | * | 10/2006 | Peric ..................... G05D 23/10 165/297 |

* cited by examiner

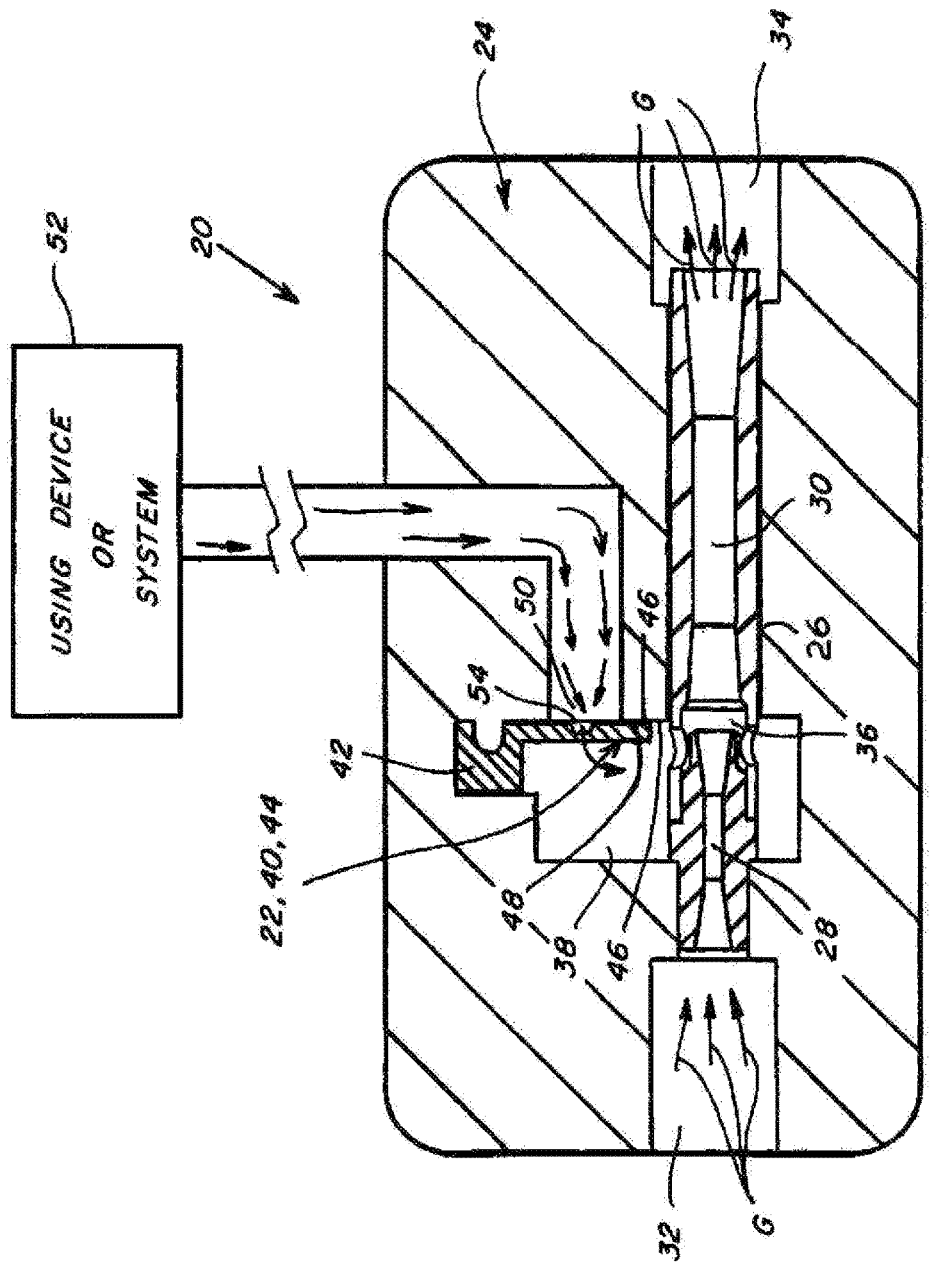

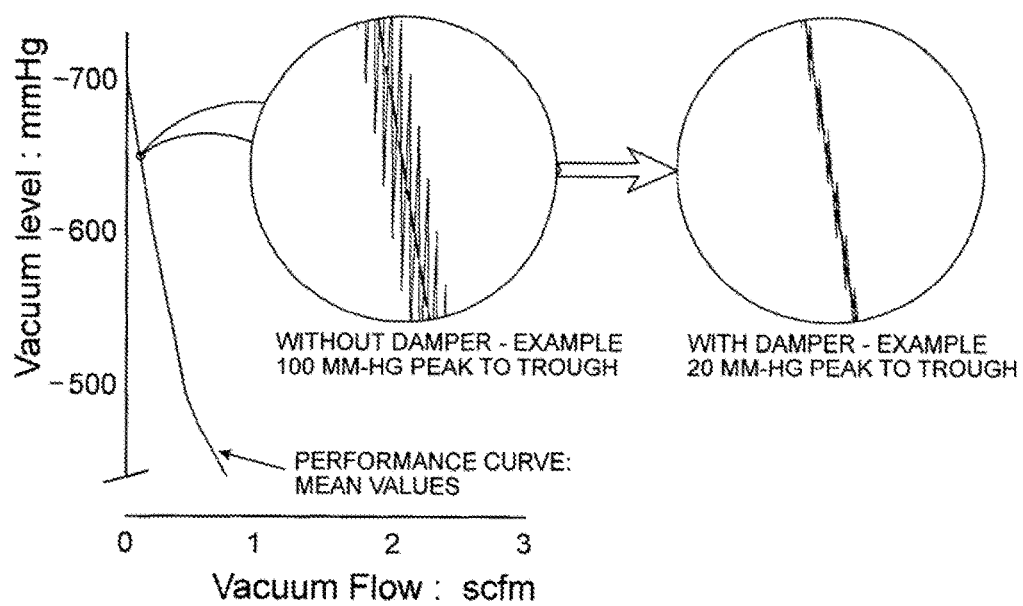

METHOD AND SYSTEM FOR ATTENUATING TRANSMISSION OF HIGH AMPLITUDE OSCILLATIONS BY A VACUUM SYSTEM

This application claims the benefit of U.S. Provisional Application No. 61/552,306, filed Oct. 27, 2011.

TECHNICAL FIELD

This invention relates generally to a method and system for attenuating or damping the amplitude of vacuum pressure oscillations in a vacuum system, and more particularly, which is self modulating to attenuate or damp high amplitude vacuum pressure oscillations to limit or prevent transmission thereof to sensitive apparatus connected to the system such as instruments and tools.

BACKGROUND ART

The disclosure of U.S. Provisional Application No. 61/552,306, filed Oct. 27, 2011, is hereby incorporated herein in its entirety by reference.

Vacuum generators that use air or another compressible gas, are well known for parts holding and pick & place applications. Within the design parameters of the vacuum generator, the maximum vacuum level attained is typically controlled by changing the inlet feed pressure of the compressed gas supply. Part release is typically obtained by turning off the inlet air supply to allow ambient air to be drawn through the exhaust nozzle to dissipate vacuum in the downstream system.

Compressible gas vacuum generators utilize a progression of gas flow nozzles for generating the vacuum. The first nozzle of a vacuum generator is configured to generate deep, maximum vacuum (greater than approximately 90% vacuum) and accomplishes this by increasing inlet air velocity to a sonic level as the feed pressure is increased and the vacuum level deepens. Until sonic velocity is approached, the induced vacuum pressure may exhibit minor low amplitude, low frequency oscillations, but is typically fairly stable overall.

Because the media is compressible gas, as deeper vacuum levels are attained, it has been observed that within a relatively narrow range of feed air pressures, random rate instability and turbulence within the vacuum generator can cause higher amplitude random rate oscillations in vacuum pressure. This period of instability is often evidenced by exhaust air noises which can be heard as rapid popping or humming or squealing noises. In aeronautical engineering literature this instability/turbulence phenomenon is well documented for aircraft as they break the sound barrier. As a rule, the vacuum generated is proportional to the velocity of the air stream in the first nozzle, and the rapid velocity oscillations have been found to be accompanied by corresponding rapid ripples and spike oscillation in the vacuum level generated, which can exceed 45 mm Hg. peak-to-trough. Because the oscillations often occur at high frequency, they do not register on a bourdon tube style vacuum gauge due to slow response time of those gauges, but can be observed with an oscilloscope.

For many industrial applications the high frequency, high amplitude vacuum oscillations are not problematic because the work pieces being held or manipulated are robust enough not to be damaged by the oscillations. Also, the attendant vacuum generator exhaust noises are often not noticed or of importance as they may be concealed by the ambient background noise of a manufacturing plant. However, high amplitude vacuum spikes can cause problems for more sensitive applications where the vacuum level must be precisely controlled, such as, but not limited to, applications such as in the medical field in which precision instruments are used and delicate parts or tissue is handled or manipulated.

Referring to FIG. 1, vacuum flow is plotted against vacuum pressure generated by a representative vacuum generator supplied by compressed air at a particular feed pressure. The resulting curve shows that the generator produces high vacuum flow at shallow vacuum levels (near atmospheric pressure) and zero or near zero vacuum or air flow, hereinafter sometimes referred to as "vacuum flow" or "air flow", at the deepest maximum vacuum level that can be attained in a sealed system. The area under the curve from atmospheric pressure to a particular vacuum level represents the power available to evacuate the volume of a system by the vacuum generator. The curve also shows several areas where irregularities caused by turbulent air flow through the first and second nozzles of the vacuum generator affect the vacuum generation, in particular, reduce it, at about −320 mm Hg. and about −520 mm Hg.

The objectionable high amplitude vacuum pressure oscillations have been found to develop as vacuum level deepens and approaches its maximum level. This region of FIG. 1 is magnified to illustrate representative oscillations in the maximum level region, and also comparatively at a shallower vacuum region. In a vacuum generator utilizing two nozzles, this effect is believed to be due to the instability of the air stream passing through the first nozzle as the compressed air is increased to sonic or near-sonic velocity in order to generate a less-than atmospheric pressure (vacuum) in the chamber between the nozzles. The oscillations were found to be most existent near the deepest vacuum, particularly between about −620 and −690 mm Hg. and can have a peak-to-peak amplitude greater than 100 mm Hg., reaching 180 mm Hg. or so. One practical application where this has been found problematic is for supplying vacuum to certain instruments for delicate surgery of the eye which require steady vacuum in this range.

One known manner to attenuate or damp the transmission of the objectionable high amplitude vacuum pressure oscillations in a vacuum system is to use flow restrictors, such as baffles and the like. However, one shortcoming to this approach is that any flow restriction or restrictions between the nozzles and the vacuum system being evacuated by the vacuum generator will reduce the available power. Any restrictions can also cause system evacuation time to increase and will reduce the responsiveness of the overall system. Fixed flow restrictors such as baffles and the like are also disadvantageous as they are always present and thus do not modulate or vary in effectiveness in response to vacuum demand or the undesirable oscillations as they arise. For some applications such as the above referenced surgical instrument application, it is important that the oscillation damping be self-modulating to provide minimal resistance to vacuum flow throughout the full range of operation of the instruments.

Although the above description is for a single-stage vacuum generator comprising a first and second nozzle in series, it should be noted that the noted shortcomings also pertain to multi-stage vacuum generators having three or more nozzles in series, and to larger capacity generators where sets of two or more nozzles are placed in parallel to obtain a greater vacuum flow rate.

Thus, what is sought is a manner of attenuating or damping the amplitude of vacuum pressure oscillations in a vacuum system, and more particularly, which is self modulating to attenuate or damp high amplitude vacuum pressure oscillations to limit or prevent transmission thereof to sensitive apparatus connected to the system such as instruments and tools.

SUMMARY OF THE INVENTION

What is disclosed is a method and system for attenuating or damping the amplitude of vacuum pressure oscillations in a vacuum using or powered system, which is self modulating to attenuate or damp high amplitude vacuum pressure oscillations to limit or prevent transmission thereof to sensitive apparatus of the using device or system such as instruments, tools, and the like. The invention may be integrated with the vacuum source, such as a vacuum generator or the like, or installed anywhere in the vacuum system, line or other flow path between the vacuum source, e.g., vacuum generator, and the using system.

According to a preferred aspect of the invention, the method and system utilize a flow-modulated damper in a vacuum flow path between a vacuum generator and the vacuum using or powered system, configured and operable to reduce the amplitude of vacuum pressure oscillations conveyed to the vacuum using device or system, e.g., instruments, tools, and other devices thereof, at very low vacuum flow at maximum vacuum, and also under deep vacuum/low flow conditions. The flow-modulated damper is additionally configured to have minimal flow restriction over the full flow range of vacuum produced by a vacuum generator, so that pertinent performance parameters such as, but not limited to, system evacuation time and vent time, are not significantly affected, including under shallow vacuum/ high flow conditions. As a result, in the deep and maximum vacuum ranges, as used here being generally in a −550 mm Hg. or higher level, vacuum pressure oscillations are reduced to a level where delicate parts and tissue can be held or manipulated without damage, and at shallower vacuum levels, flow and response are not significantly reduced. As an example of a practical application, in the medical field, and in surgery of the eye in particular, it is important for the surgeon to have precise vacuum pressure and to have deep vacuum delivered to the surgical instruments with minimum amplitude oscillations and good response time.

In testing, the invention has been shown to reduce the vacuum oscillations by a factor of two-thirds and more in certain of those applications. For example, in a system wherein undamped oscillations can be found at 100 mm Hg. and reach as high as 180 mm Hg. peak to trough amplitude, use of the self-modulating damper of the invention has been found to reduce that amplitude to consistently as low as 20 mm Hg.

According to another preferred aspect of the invention, the flow-modulated damper can be integrated into a housing that includes the vacuum generator, or it can be integrated into. e.g., plumbed, into a system as a stand-alone component in a vacuum flow path between the vacuum generator and vacuum using or powered device or system. The damper comprises an elongate element or member of a rubber or rubber-like polymer having resilient flexibility and a flat longitudinally extending surface. As a non-limiting example, the member can have a generally rectangular cross sectional shape. The element is constrained at one longitudinal end, and has an opposite free end, which in combination with the resilient flexibility enables it to function in the manner of a tongue. An intermediate portion of the element between the two ends is disposed over a port that connects the vacuum generator with the vacuum using system. The structure surrounding the port preferably forms a substantially flat surface or seat. The element, when in its flat free or unmodulated state, that is, unflexed, it is disposed in a closed position in covering relation to the port and lays against or contacts the seat around the periphery of the port, to form a substantially sealed condition thereabout, except for at least one small vacuum orifice which extend through a peripheral interface between the element and the seat, from the edge of the element to the edge of the port.

The at least one small vacuum orifice is sufficiently configured in at least size, such that when the element is closed against the seat, it is capable of communicating a low vacuum or air flow level at deep vacuum from a using system connected to the port, but is insufficient in size to permit greater flow without modulating or opening. The shape, size and location of the vacuum orifice or orifices can be configured to provide a desired or metered level of low flow, and can be incorporated into the damper only; into the seat only; or partially in both the damper and the seat. As non-limiting examples, the orifice can be formed in the damper and/or seat by molding or machining. Also, it has been found that neither the orientation or location of the orifice with respect to the vacuum source is critical, which is desirable as it enables using the damper at about any location between a vacuum source and a using device or system, including in a chamber or plenum of a flow path adjacent to the vacuum source or generator or in a line connecting the generator with the using system. Still further, as noted above, the invention utilizes at least one of the small vacuum orifices, and they can be provided in a variety of configurations, as desired or required for a particular application.

According to another preferred aspect of the invention, when the damper is in the unmodulated or closed position under low flow conditions at deep vacuum, the resilient property of the damper combined with the small size of the vacuum orifice or orifices has been found to substantially damp and limit amplitude of pressure oscillations through the orifice or orifices. This is advantageous, as it enables use of a variety of instruments and tools that are sensitive to or affected by such oscillations and require only minimal vacuum flow under deep vacuum conditions. Also advantageously, obstructions such as baffles or flow restrictors are not required in or about the orifice or orifices for preventing transmission of high amplitude vibrations, either from the vacuum generating side or the using side, such that that vacuum flow and response are not unacceptably affected or degraded under the no or low flow conditions.

According to another preferred aspect of the invention, the flow-modulating capability is provided or facilitated by the characteristics of the damper, namely, a combination of the restraint of the damper at only one end, its resiliently flexibility, and the presence and configuration of the vacuum orifice or orifices. Essentially, with the damper unmodulated or closed, if flow through the small orifice, or orifices, is inadequate to meet demand, vacuum condition in the port and on the port side of the damper will be different, that is, shallower, than those on the vacuum generator side of the damper. As long as this differential vacuum condition exists, it will exert a resultant force on the damper, in a direction toward the deeper vacuum or lower pressure side, that is, away from the port. When this force is sufficient, the damper will responsively resiliently yield or flex, so as to break contact with at least a portion of the seat about the port and open to a certain extent which will be a function of the differential vacuum condition and characteristics of the damper. The opening of the damper will communicate vacuum flow from the port to at least one portion or region of the periphery of the damper, from where the air will flow toward the region of the lowest or deepest vacuum, generally toward the vacuum generator.

The configuration and/or composition of the damper is selected such that when the damper is resiliently flexed or modulated, internal stresses will be generated within the damper, urging it to return to the flat or free state (unmodulated). These internal stresses will be in opposition to the external forces exerted by the differential vacuum condition. As a result, when modulated the damper will automatically flex to an extent or position wherein the internal stresses will equal the external forces. Because many factors or condition can change at any time, including, but not limited to, vacuum usage by the using system, generation, temperature and other environmental conditions, external forces exerted against the damper may be very dynamic, and the damper will responsively flex or modulate, in a manner seeking to achieve equilibrium between the external forces and internal stresses acting on it. In this regard, the resilient flexibility of the damper, dimensions and structural features thereof, as well as distance from the port to the constrained end, volume of regions or cavities on both sides of the damper, and port size and configuration, can be selected to achieve desired or required modulation characteristics. As one non-limiting example in this regard, the damper can be of one piece, uniform flat construction. As another example, the damper can include one or more grooves, ribs, or other structural features that will influence the manner of flexure thereof, e.g., more toward the free end verses toward the constrained end, more curvature or less, that can influence modulation characteristics reactive to flow and differential vacuum conditions.

To explain further, the extent to and manner by which the damper will flex and open will be a function of the construction of the damper, which will be a constant, and the external forces and internal stresses generated by differential vacuum conditions, and flow through the vacuum port. As air (or other gases or vapors) flows between the surface of the damper and the seat or other adjacent surfaces, the surface area of the damper exposed to the shallower vacuum, may be increased, which can flex the damper to a greater extent or in a different manner compared to lesser flow conditions, until equilibrium is reached. If steady flow conditions are present, the damper is operable to maintain a steady flexed position, and the resilient property of the damper enables it to store the energy that it absorbs as the internal stresses, which will then be released to reduce the degree of flexure or return the damper to the flat or closed (unmodulated) condition, which like the flexure, will be a function of the vacuum flow through the damper. As a result, the damper is self modulating in both the opening and closing directions responsive to flow.

As another preferred aspect of the invention, the self modulating capability and flexure characteristics of the damper can be selected to provide rapid or slow response to dynamic conditions, as desired or required for a particular application. The self modulating characteristics can also be configured to enable the damper to flex to an infinite number of positions between the unmodulated or fully closed or flat position and its fully flexed position responsive to a wide range of flow conditions that can rapidly change.

As still another feature of the invention, the resilient composition and configuration of the damper enable it to absorb and damp a significant portion of any high amplitude pressure oscillations in proximity thereto, particularly when the damper is open. In regard to configuration, the attachment of the damper at only one end, and its resulting tongue like operability when open, presents a wedge shaped entrance region between the vacuum generating source and the port. This wedge shaped region is bounded on one side by the surface in which the port is located, and on the opposite side by the resiliently flexible damper. This configuration has been found to advantageously damp a substantial portion of any high amplitude pressure oscillations that enter that region, especially at lower flow rates under deeper vacuum conditions when the damper is only partially open and the wedge shaped area is relatively small in extent between the surface of the damper and the opposing surface, such that transmission of the pressure oscillations through the port to the using system or device is reduced markedly under the lower flow conditions, which is a particularly sought after feature for applications wherein sensitive instruments and tools are to be used.

Thus, the combination of a vacuum generator and flow-modulated damper, are configurable according to the invention to provide a vacuum delivery system responsive to dynamic conditions, that attenuates or damps unwanted pressure disturbances under deep vacuum, no and low flow conditions, to provide steady, high quality vacuum to an instrument or instruments or other vacuum using or operated devices connected to the system.

BRIEF DESCRIPTION OF THE DRAWINGS

FIG. 4 is a sectional view of the housing, showing elements of the vacuum system, including the vacuum generator and the flow-modulated damper in an unmodulated or closed position which communicates only low levels of vacuum flow (denoted by small arrows) from a using device connected to the system through a small vacuum orifice of the damper;

FIG. 12 is a graphical representation of vacuum level (pressure) verses vacuum for a vacuum system, illustrating in a first balloon representative undamped amplitude of vacuum pressure oscillations in the deep vacuum range generated during operation of the system, and in a second balloon representative reduction in amplitude of the oscillations achieved using the flow-modulated damper of the invention

DETAILED DESCRIPTION OF THE INVENTION

Figure 1:
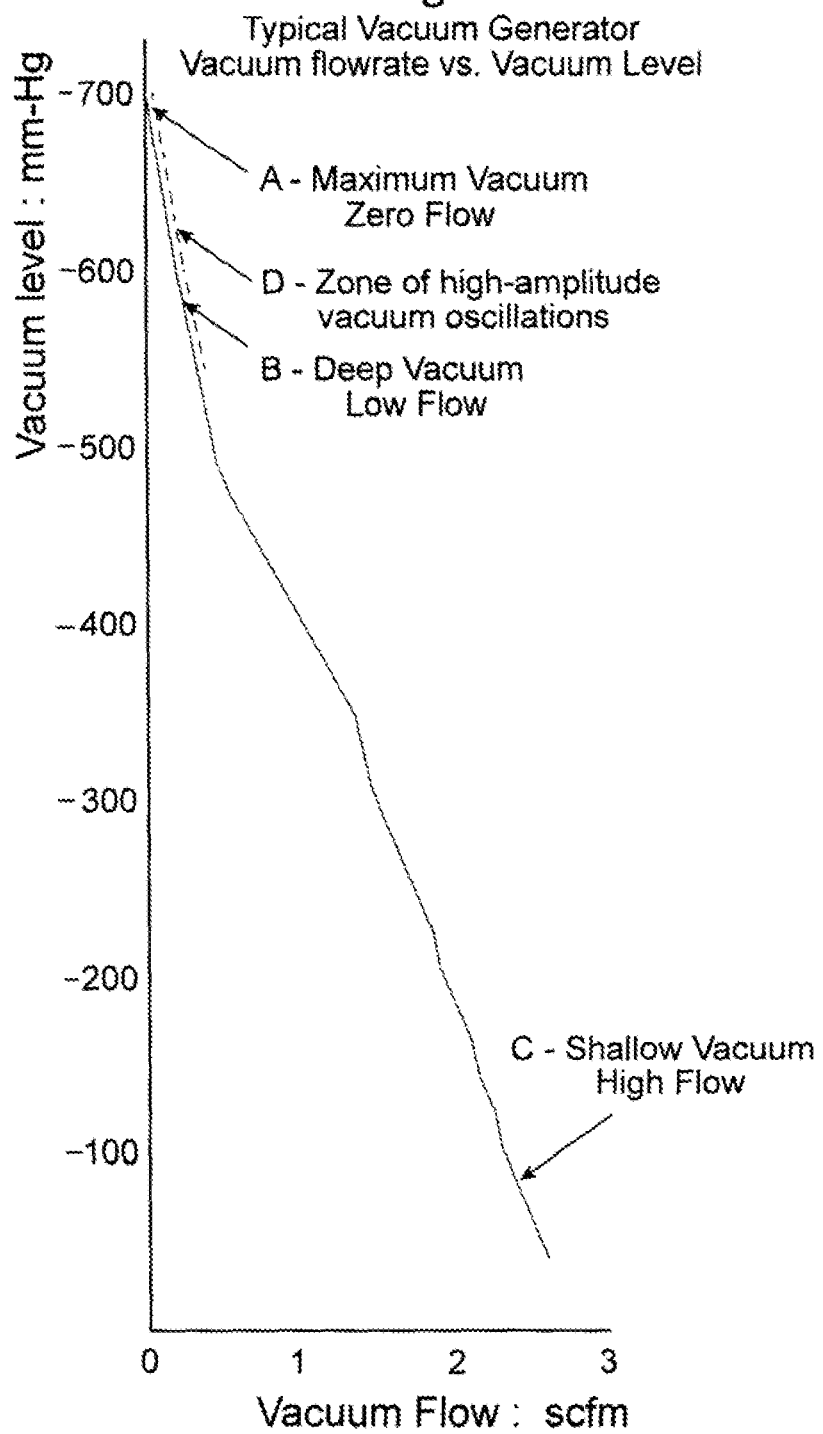
FIG. 1 is a graphical representation of vacuum level verses vacuum flow rate for a typical vacuum generator of a type capable of providing a range of air or gas flow rates at vacuum levels ranging from shallow to deep.

Referring now to the drawings, wherein preferred embodiments of the invention are illustrated, as discussed above, FIG. 1 is a graphical representation of vacuum level verses vacuum flow rate for a typical vacuum generator of a type typically utilized for providing vacuum to devices such as, but not limited to, instruments and tools for performing surgery on sensitive tissue such as the human eye. Such instruments commonly require relatively deep vacuum, e.g., more than about −550 mm Hg., at very low flow rates, as well as higher flow rates at shallower vacuum, e.g., under about −500 mm Hg. Three representative levels of vacuum demand are denoted by letters A, B and C. As also discussed above, a common problem encountered when using such sensitive instruments and tools is that disturbances in the vacuum flow commonly generated at deep vacuum conditions can be undesirably transmitted through the vacuum generation system to the instrument or tool. In particular, such disturbances of greatest concern include high amplitude pressure oscillations typically encountered at deep vacuum, low flow conditions, generally denoted by region D.

Figure 2:
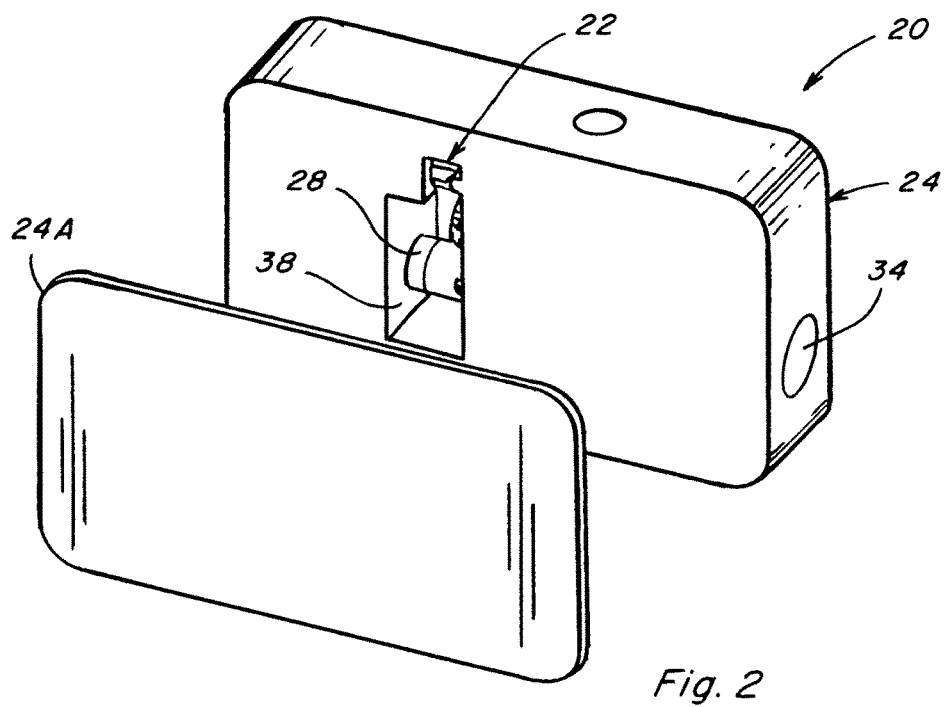
FIG. 2 is a perspective view of apparatus of a system of the invention, including a housing with a cover panel removed to reveal a plenum, vacuum generator and flow-modulated damper of the system.
Figure 3:
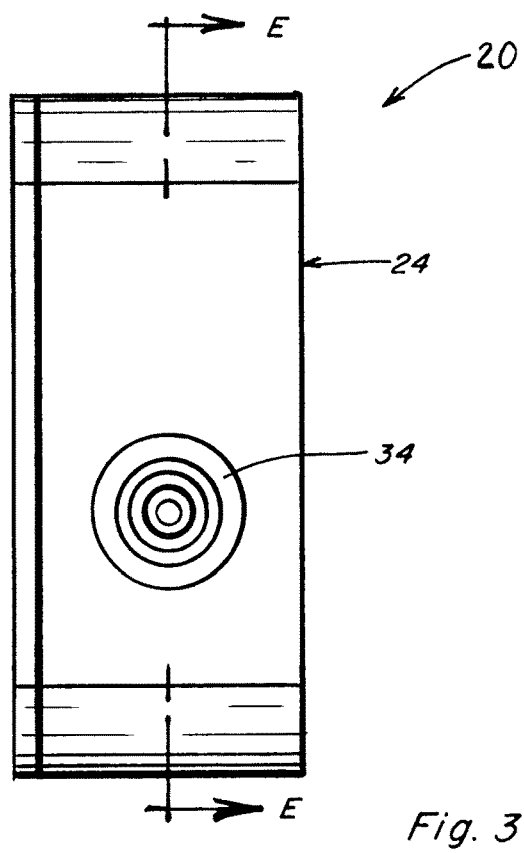
FIG. 3 is an end view of the housing of FIG. 2 showing an exhaust port of the system.

Referring also to FIGS. 2 through 6, apparatus 20 of a system of the invention for attenuating or damping the amplitude of vacuum pressure oscillations in a vacuum system, is shown. Apparatus 20 includes a flow-modulated damper 22 that is integrated into a housing 24, along with a vacuum generator 26 including a first nozzle 28 and a second nozzle 30 disposed in a passage through housing 24 between an inlet port 32 that will be connected to a source of pressurized gas, such as air or another suitable gas or a mixture of gases (herein referred to collectively as "air"), and an exhaust port 34 through which the gas will be exhausted from the system. Housing 24 can be formed, for instance, of a suitable substantially rigid material such as a metal or plastics, with the required features molded or machined therein, and can include an optional removable service panel or cover 24A, as illustrated in FIG. 2. Nozzle 28 has a converging internal flow passage through which the pressurized gas (denoted by arrows G in FIG. 4, flows, that increases the velocity of the gas stream flowing across a gap 36 between nozzles 28 and 30, just before the stream enters nozzle 30. In accordance with Bernoulli's principle, the gas stream causes a sub-atmospheric pressure (vacuum) in and adjacent plenum or chamber 38 in connection with 36. The gas stream expands and slows as it passes through nozzle 30 then exhausts to atmosphere through port 34.

The flow-modulated damper 22 includes a flexible element 40 preferably constructed of a resiliently flexible material, such as, but not limited to, a rubber or rubber-like polymer material, having a first end 42 constrained at one end in a cavity formed by housing 24 adjacent to chamber 38, and an opposite second end 44 located in chamber 38. Second end 44 preferably has an elongate shape with a thin cross section relative to its length, so as to have opposite, longitudinally extending surfaces, at least one of which preferably is flat. Second end 44 in its free state is substantially straight, so as to be capable of conforming to a straight flat surface, when placed in abutment therewith, and is freely flexible, so as to be capable of flexing away from the surface at an acute angle thereto, essentially in the manner of a tongue. The composition and structure of flexible element 40, including the shape and dimensions of second end 44, can be selected to provide desired flexibility characteristics for a particular application.

Figure 4A:
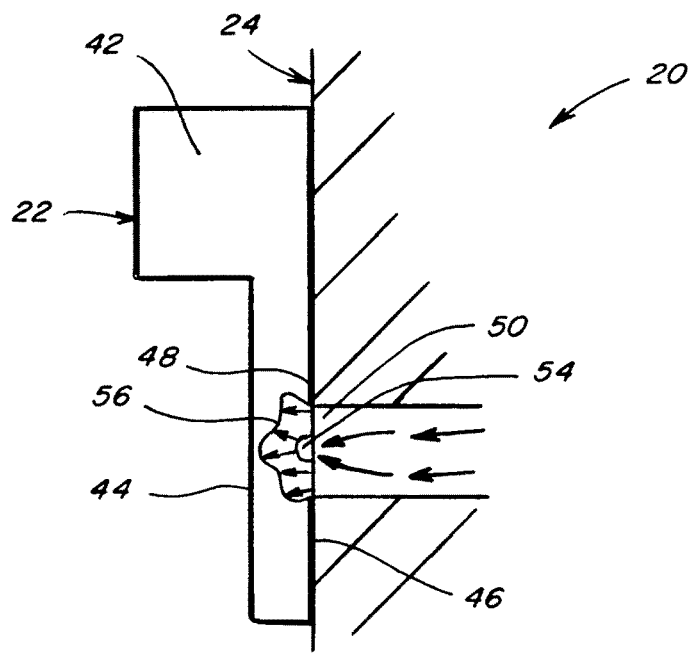
FIG. 4A is a simplified partial fragmentary sectional view of the housing and damper in the unmodulated or closed position, illustrating with arrows external forces exerted thereagainst by a differential vacuum condition.

Referring more particularly to FIGS. 4 and 4A, second end 44 of element 40 is positioned such that a flat longitudinally extending surface 46 surface thereof, in its free or unmodulated state, is positioned to lay against or abut an internal surface of housing 24 bounding chamber 38, which serves as a seat 48. Seat 48 is similarly flat and further extends about one end of a vacuum port 50 of a vacuum flow path of the system. The other end of vacuum port 50 connects with a using system or device 52, which can comprise, but is not limited to a vacuum powered tool or instrument used for surgery of the eye or the like.

In the embodiment shown, flexible element 40 is positioned and configured such that in the unmodulated condition or state an intermediate portion of second end 44 is disposed over port 50 and lays against or contacts seat 48 around the periphery of the port, to form a substantially sealed condition thereabout. Second end 44 further includes small vacuum orifices 54, here on opposite sides of the damper, each of which extends through a peripheral interface between the damper and seat 48 (see FIGS. 10 and 11 also), from the edge of the damper to at least the edge of the port, to communicate port 50 with chamber 38 in connection with vacuum generator 26.

Each vacuum orifice 54 is sized and configured such that when flexible element 40 is unmodulated so as to lay against seat 48, it is capable of communicating a low vacuum flow level at deep vacuum from a using device or system, represented by system 52 shown connected to port 50, but is insufficient in size to permit greater flow. To provide this capability it can be observed that the sectional flow area through each vacuum orifice 54 (and collectively through both orifices 54) is substantially smaller than a sectional flow area through port 50. Here, as noted above, each vacuum orifice 54 is located in a side of second end 44 of the damper, to provide a desired or metered level of low vacuum flow from using system 52 under deep vacuum conditions. When flexible element 40 is in the closed position under these conditions, the resilient property combined with the small size of orifices 54 damps and limits transmission of high amplitude pressure oscillations through the orifices without need for obstructions such as baffles or flow restrictors that can reduce responsiveness at low flow conditions. As an example, the configuration of damper 22 shown, which is representative of both of the embodiments shown in FIGS. 10 and 11, has been found to reduce the amplitude of oscillations substantially, e.g., down to as low as 20 mm Hg. compared to as greater than 100 mm Hg. Undamped, as illustrated graphically in FIG. 12.

Referring in particular to FIGS. 4 and 4A, flow-modulated damper 22 is shown with second end 44 of flexible element 40 in a flat position and configuration, that is, unmodulated, abutting or laying against and forming a substantially sealed condition with seat 48 except for the flow communicated therebetween through vacuum orifices 54. Here, due to this substantially sealed condition, only very low flow, as denoted by the small arrows, or no flow occurs between the using system or device, represented by device 52, which is representative of flow conditions in the area of the graph of FIG. 1 denoted by letter A.

When element 40 is unmodulated or closed, if vacuum flow through orifices 54 is inadequate to meet vacuum demand of the using system or device, pressure in port 50 will increase, that is, the vacuum condition in port 50 will be shallower, than that in chamber 38 on the vacuum generator side of element 40. This will result in a differential vacuum condition between chamber 38 on one side of element 40, and port 50 on the other side, which will exert a force on element 40, in a region of surface 46 generally corresponding to the location and shape of port 50, in a direction toward the deeper vacuum or lower pressure side, that is, away from port 50, as denoted by force arrow array 56.

Figure 5A:
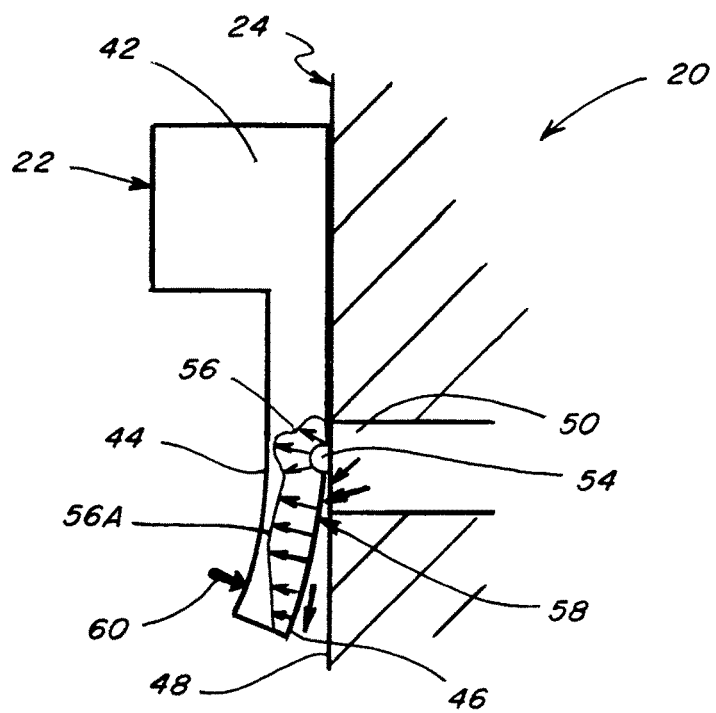
FIG. 5A is another simplified partial fragmentary sectional view of the housing, showing the damper in the partially open position, illustrating again with arrows external forces exerted thereagainst by a differential vacuum condition resulting from the higher level of flow.
Figure 5:
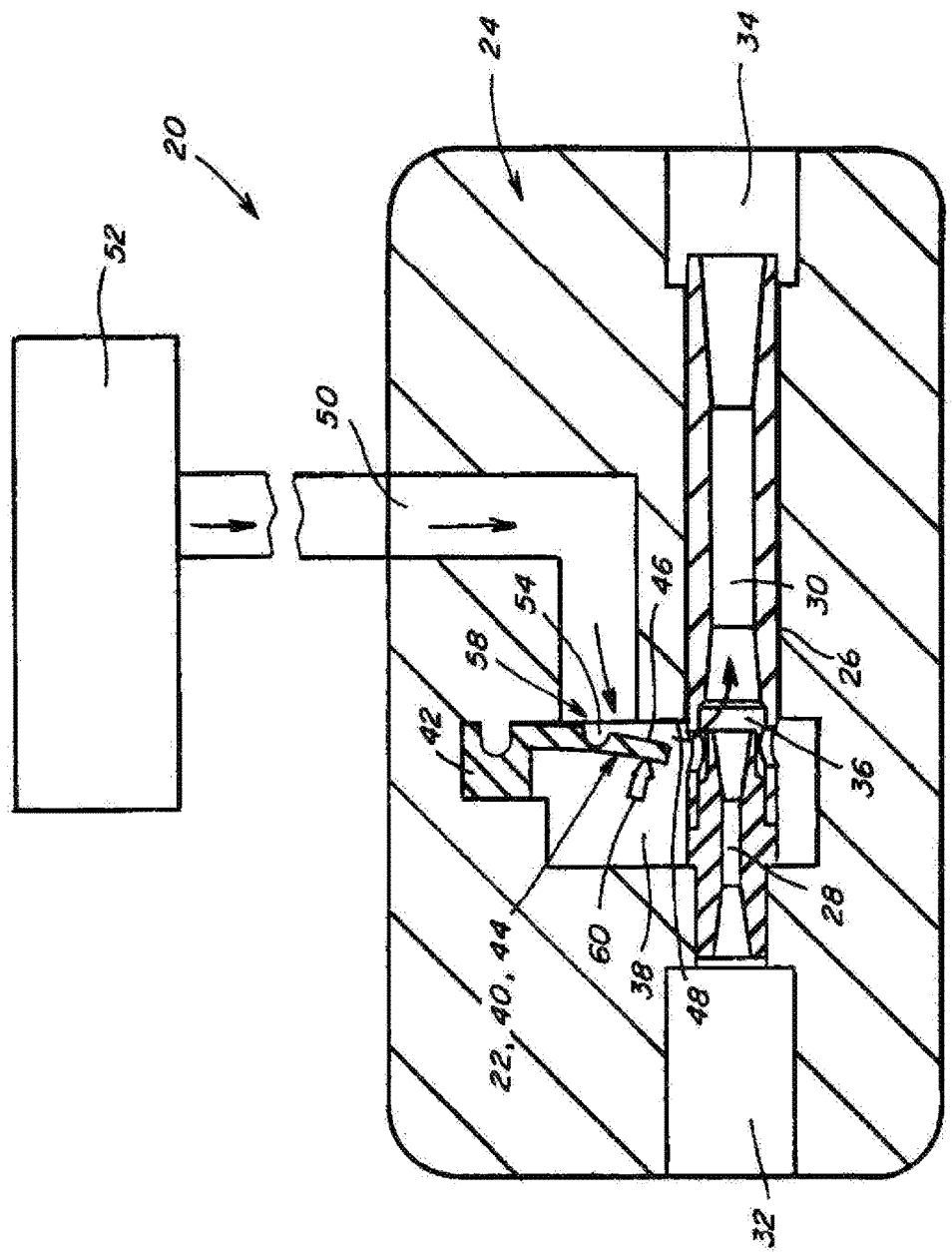
FIG. 5 is another sectional view of the housing, vacuum generator, and the flow-modulated damper in a partially open position, representative of the configuration of the system for a higher but still relatively low level of flow, denoted by larger arrows.

Referring more particularly to FIGS. 5 and 5A, if the differential vacuum condition increases sufficiently, the resulting force acting on element 40 will increase sufficiently to cause element 40 to responsively modulate, by resiliently yielding or flexing, so as to break contact with at least a portion of seat 48 and open to a certain extent, as denoted by numeral 58. Opening 58 provides a path for vacuum or air flow between surface 46 and seat 48, from port 50 to at least one portion or region of the periphery of element 40, from where the air will seek the region of the lowest or deepest vacuum, generally toward vacuum generator 26, as denoted by the heavier arrows. This flexure is facilitated by the configuration and composition of element 40. When opening 58 is present, the region of surface 46 of flexible element 40 against which the external forces of the shallower vacuum (higher pressure) condition are exerted will increase, as denoted by enlarged force array 56A in FIG. 5A. The forces can vary in degree and location, as a function of the location of opening 58, level of vacuum flow, velocity thereof, and other factors. This is representative of the position and configuration of flexible element 40 under deep vacuum, low vacuum or air flow conditions as generally identified by region B of the graph of FIG. 1. Under these conditions, vacuum oscillations can cause using system or device problems, but the position and configuration of flexible element 40 provide maximum oscillation damping effect while still not restricting vacuum flow.

As a result of the flexure, internal stresses will develop within flexible element 40, denoted by arrow 60 (shown externally of the flexible element due to its small size). Internal stresses 60 oppose external forces 58, and an equilibrium condition therebetween will be reached, with the flexible element being flexed in a corresponding manner reflecting the distribution of forces and internal stresses. The flow conditions may be dynamic to varying extents, or more static. If conditions are dynamic, distribution of forces can vary, such that the shape and/or degree of flexure of flexible element 40 may vary considerably. If conditions are more steady state, flexible element 40 can maintain a more constant flexed shape and/or position. When flexed, the resiliency or elasticity of flexible element 40 enables it to store the energy of internal stresses 60 urging it to return to its flat shape and position. When the flow conditions lessen, the external forces will be reduced, and flexible element will release a corresponding proportion of internal stresses 60 to reduce the degree of flexure thereof and the size of opening 58. Thus, damper 22 is self modulating in both the opening and closing directions responsive to flow.

Because many factors or condition can change at any time, including, but not limited to, vacuum usage by the using system or device, generation, temperature and other environmental conditions, external forces 58 exerted against flexible element 40 may be very dynamic, and the flexible element will responsively flex or modulate, in a manner to reach equilibrium between the external forces and internal stresses 60.

Figure 6:
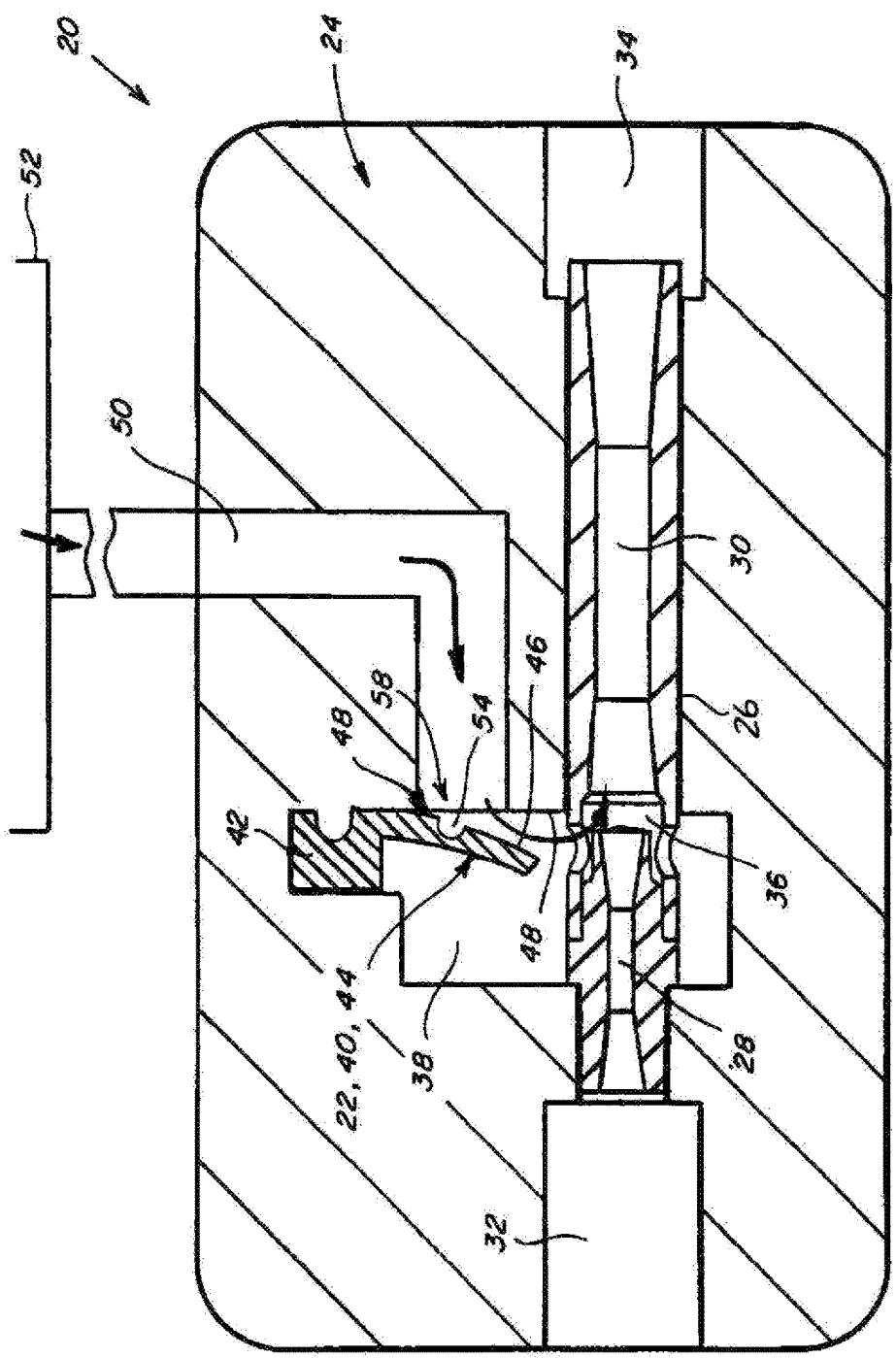
FIG. 6 is another sectional view of the housing, vacuum generator, and the flow-modulated damper in a more fully open position, representative of the configuration of the system for a still higher level of flow, denoted by still larger arrows.

Referring more particularly to FIG. 6, increased flexure of flexible element 40 to a more fully open position is illustrated, responsive to greater vacuum flow from using device 52 to vacuum generator 26, as denoted by the heavier arrows. Here, the size of opening 58 is significantly larger, and there is greater curvature of flexible element 40, which is indicative of greater external forces acting on the flexible element resulting from the flow. This is representative of the position and configuration of flexible element 40 under shallow vacuum, high air flow conditions, about as illustrated at location C on the graph of FIG. 1. Under these conditions vacuum oscillations are not an issue and the fully or nearly fully open damper 22 causes minimal flow restriction so vacuum flow is maximized and system evacuation time is minimized.

The resilient flexibility of flexible element 40, dimensions and structural features thereof, as well as distance of port 50 to constrained end 42, volume of chamber 38 and port 50, and the configurations thereof, can be selected to achieve desired or required flow and modulation characteristics. As a non-limiting example, second end 44 of flexible element 40 can be of one piece, uniform flat construction, with the exception of vacuum orifice or orifices 54, which can be located on only one side of the flexible element, or on two or more sides, to communicate vacuum or air flow from two or more sides of the flexible element. The location of orifice or orifices 54 at an intermediate position between the ends of end 44 of flexible element 40 can also serve to reduce the cross sectional extent thereof, which can facilitate flexure of the flexible element at that location, as will be discussed in reference to FIGS. 10 and 11 below. Additionally, end 44 can include one or more grooves, ribs, or other structural elements to further influence or change the manner or degree of flexure thereof, e.g., to increase flexure more toward the free end verses toward the constrained end, or to increase or decrease the radius of curvature, to influence modulation characteristics reactive to flow and differential vacuum conditions in a desired manner.

The resilient composition and configuration of flexible element 40 additionally enable it to absorb and damp a significant portion of any high amplitude pressure oscillations, particularly when the flexible element is unmodulated and closed, or partially modulated and open, as represented in FIGS. 4, 4A, 5, and 5A. In particular, in the unmodulated state, the rubber or rubbery material of element 40 bounds one side of each vacuum orifice 54, the other side being the seat 48, such that pressure oscillations are damped or attenuated by impinging the rubber or rubbery surface bounding the orifices 54. In the partially modulated state, the oscillations are damped first by impinging surface 46 of flexible element 40 which absorbs and attenuates pressure spikes. When the flexible element is open so as to form wedge shaped opening 58, the pressure spikes are deflected by the geometry of the opening outwardly toward chamber 38 and away from port 50. As the pressure waves expand outward, the wave amplitude is decreased so the oscillations are effectively dispersed and damped. Additionally, as can be best seen in FIGS. 4A and 5A, surface 46 extends a significant distance past port 50. This can be advantageous to provide additional surface area for deflecting, absorbing, and attenuating the pressure spikes. This additional extent can be tailored, as desired or required to achieve desired damping effect.

In particular with regard to FIGS. 5, 5A, and 6, it can be observed that flexible element 40 is oriented and positioned to extend longitudinally toward gap 36 of vacuum generator 26, and such that the free end of second end 44 of flexible element 40 is disposed closely adjacent to that gap. This is advantageous as it aligns flexible element 40 and wedge shaped opening 58 longitudinally with the most direct vacuum flow path between port 50 and gap 36, such that pressure waves emanating from gap 36 toward port 50 and entering the wedge shaped opening will be exposed to the maximum damping effect of the invention.

Figure 7:
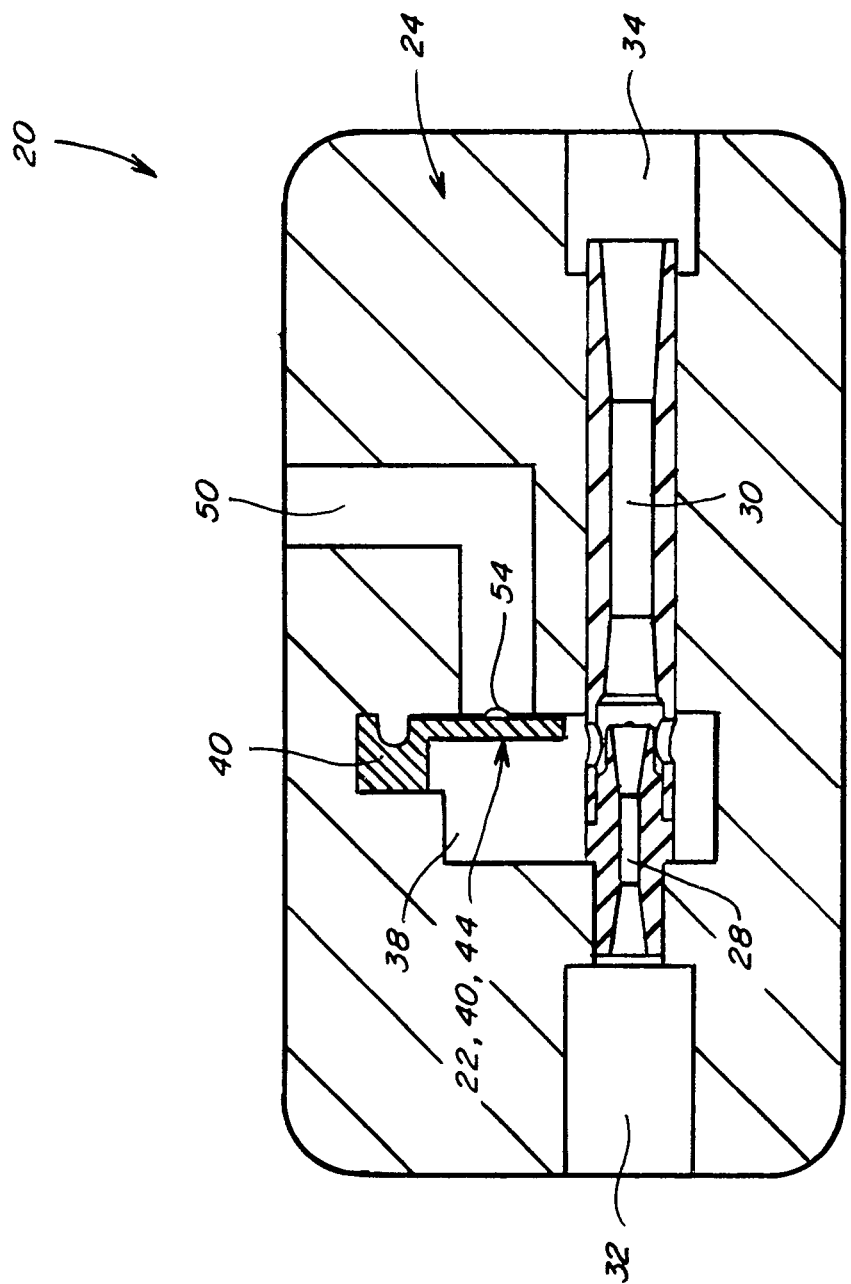
FIG. 7 is another sectional view of the housing, vacuum generator, and the flow-modulated damper, showing an alternative embodiment of a vacuum orifice of the damper.
Figure 8:
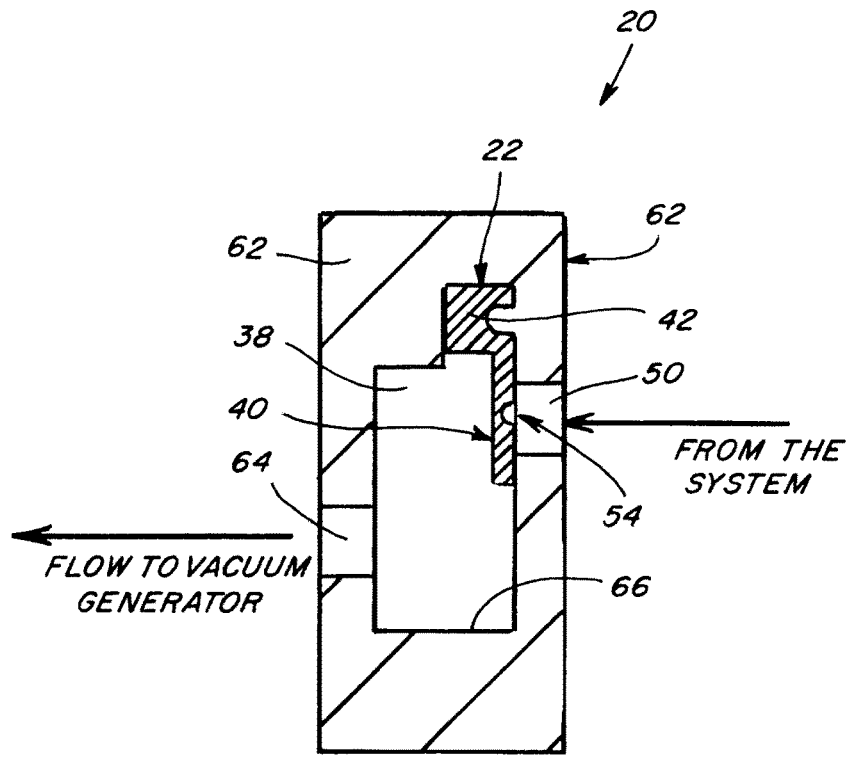
FIG. 8 is a sectional view of an alternative embodiment of apparatus of the vacuum system of the invention.
Figure 9:
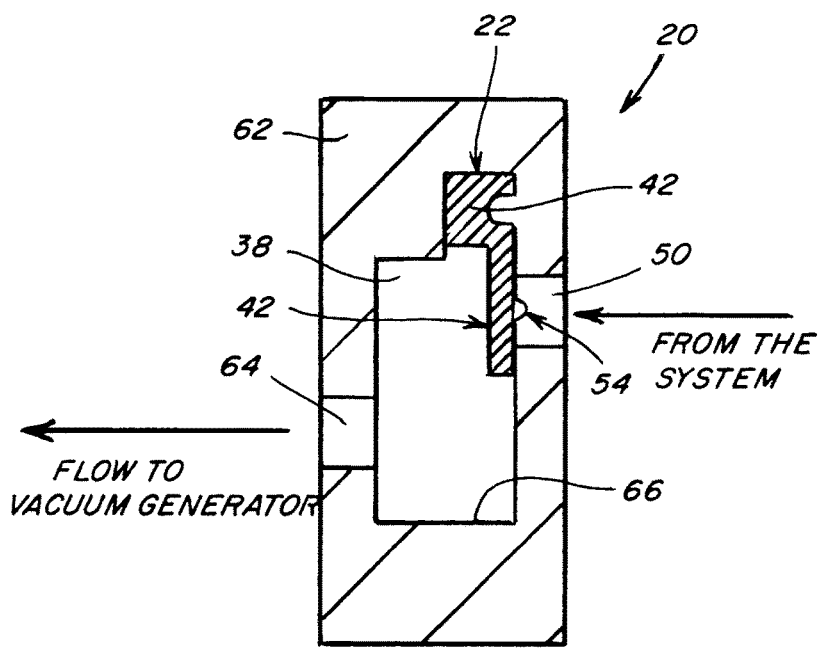
FIG. 9 is a sectional view of another alternative embodiment of apparatus of the vacuum system of the invention.

Referring also to FIGS. 7, 8, and 9, several alternative embodiments of apparatus 20 of the invention are shown. In FIG. 7, flow-modulated damper 22 is configured slightly differently by locating vacuum orifice or orifices 54 in an edge or lip on the periphery of vacuum port 50, instead of formed in second end 44 of flexible element 40 as in the embodiment of FIGS. 4, 4A, 5, and 5A. Otherwise, nozzles 28 and 30, ports 32 and 34 and chamber 38 are configured as discussed above. This location of orifice or orifices 54 provides similar or the same vacuum generation, operation and damping as just explained.

In the embodiments of the invention of FIGS. 8 and 9, flow-modulated damper 22 is contained in an inline housing 62, which will be connected between a vacuum generator, such as generator 26 of the previous FIGS., and a using system or device, as illustrated by the flow arrows. Housing 62 includes a vacuum generator port 64 and a vacuum port 50 for connection via suitable lines or plumbing to the vacuum generator and the using system, respectively. Flexible element 40 is located in the same relation to vacuum port 50 as in the previous embodiments, but vacuum generator port 64 is in a different location than gap 36 of vacuum generator 26 of the embodiments discussed above, but is still adjacent to the free end of second end 44 of flexible element 40. Alternatively, port 64 can be located in other surfaces of housing 62, such as surface 66, and chamber 38 can be dimensioned differently, as desired or required for achieving sought after vacuum power and/or damping characteristics for a particular application.

Essentially, the only difference between the embodiments of FIGS. 8 and 9 is the location of small vacuum orifices 54, which is in second end 44 of flexible element 40 in FIG. 8, and in the edge of housing 62 bounding port 50. Damper 22 of both embodiments will operate in substantially the same manner as described above, to provide flow-modulated vacuum to the using system or device, while damping transmission of high amplitude pressure oscillations to the using system or device under deep and maximum vacuum and low flow or no flow conditions.

Figure 10:
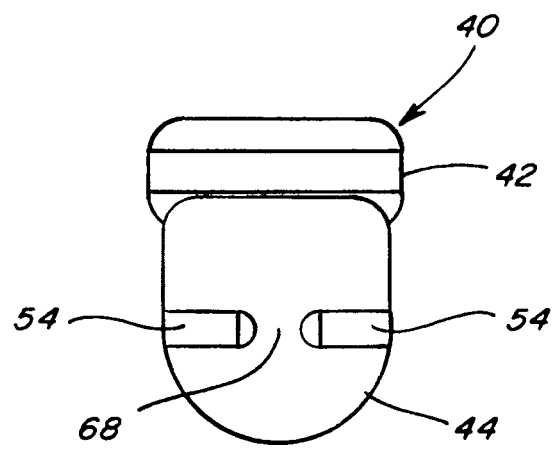
FIG. 10 is a plan view of one embodiment of a damper of the invention.
Figure 11:
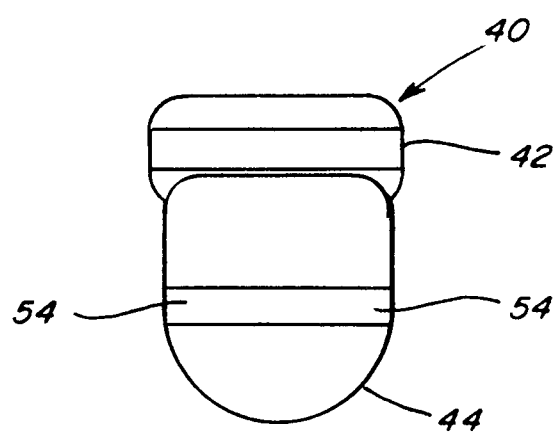
FIG. 11 is a plan view of another embodiment of a damper of the invention.

Referring also to FIGS. 10 and 11, alternative embodiments of flexible element 40 are illustrated. First end 42 of the flexible elements is the same for both versions. Both flexible elements include small vacuum orifices 54 in opposite sides of second end 44. However, in the version of FIG. 10, vacuum orifices are separated, such that the flexible element forms a rib 68 that acts to stiffen the flexible element at that location. In contrast, in the version of FIG. 11, orifices 54 connect, or extend completely across the flexible element, such that it is more easily flexed at that location, more in the manner of a hinge, whereas the version of FIG. 10 can be expected to flex in a more curvaceous manner at this location. As a non-limiting example, the more easily flexed version of FIG. 11 may have more utility or responsiveness at lower differential pressures, or when a greater amount of air or gas flow is desired for a particular differential pressure.

Referring also to FIG. 12, a graphical representation of vacuum level verses vacuum flow for a vacuum system at deep vacuum, low flow, is shown. In the balloon on the left, typical undamped vacuum pressure oscillations under deep vacuum of between about −550 mm Hg. and about −700 mm Hg., and low flow conditions, having a representative peak-to-trough amplitude of about 100 mm Hg., are illustrated. In the balloon on the right, the deep vacuum pressure oscillations are illustrated, damped using a flow-modulating damper of the invention as shown in FIG. 4. It can be observed in the illustrations of the balloons of FIG. 12, that amplitude of the oscillations is reduced to about 20 mm Hg.

As another advantage of damper 22 of the invention, vacuum orifice or orifices 54 will allow flow in both directions, that is, as vacuum flow from the using system or device to the vacuum chamber or generator, and in the reverse direction, so when the air supply is removed from inlet port 32, system vacuum will be vented by atmospheric air flowing into port 34, through nozzle 30 and into chamber 38, through vacuum orifice or orifices 54 and into vacuum port 50.

Here, it should be noted that vacuum orifice 54 is depicted larger than its actual size so as to be easily visible, but in practice will be substantially smaller, its actual size to be determined as a function of vacuum flow requirements of a using device or system and other application parameters. It should also be noted that orifice or orifices 54 can be incorporated completely into flexible element 40; completely in seat 48; or partially in each, as desired or required for a particular application. Additionally, although vacuum orifices 54 are depicted herein as being located in the side of flexible element 40 or a corresponding location on seat 48, alternatively, they or an additional orifice 54 can be located in another surfaces of the flexible element or seat, as desired or required for a particular application.

In light of all the foregoing, it should thus be apparent to those skilled in the art that there has been shown and described a method and system for attenuating or damping the amplitude of vacuum pressure oscillations in a vacuum system using a flow modulated damper. However, it should also be apparent that, within the principles and scope of the invention, many changes are possible and contemplated, including in the details, materials, and arrangements of parts which have been described and illustrated to explain the nature of the invention. Thus, while the foregoing description and discussion addresses certain preferred embodiments or elements of the invention, it should further be understood that concepts of the invention, as based upon the foregoing description and discussion, may be readily incorporated into or employed in other embodiments and constructions without departing from the scope of the invention. Accordingly, the following claims are intended to protect the invention broadly as well as in the specific form shown, and all changes, modifications, variations, and other uses and applications which do not depart from the spirit and scope of the invention are deemed to be covered by the invention, which is limited only by the claims which follow.

What is claimed is:

1. A vacuum system, comprising:
a vacuum source configured and operable to generate vacuum pressure;
an enclosed vacuum flow path for connecting the vacuum source to a vacuum using device or system for communicating the vacuum pressure thereto and vacuum flow therefrom, the flow path extending through a chamber enclosed by a housing containing a nozzle of the vacuum source or a vacuum generator port communicating with the vacuum source, at a predetermined first location in the chamber; and
a minimally flow restrictive flow-modulated vacuum pressure oscillation reducing damper disposed in the vacuum flow path within the chamber between the nozzle of the vacuum source or the vacuum generator port communicating with the vacuum source, and the vacuum using device or system, configured to communicate the vacuum pressures to the vacuum using device or system and to allow the vacuum flow therefrom under all conditions, configured to be modulated responsive to the vacuum flow and flexible so as to open the path proportionally to an amount of the flow over a full range of the generated vacuum pressures, and to be at least substantially unmodulated responsive to low vacuum flow conditions within a range between about zero and about 1 cubic foot per minute, accompanied by a vacuum pressure in a range of between about −550 mm Hg and about −700 mm Hg, the damper comprising a restrained mounting portion and a resiliently flexible tongue extending from the mounting portion and having a free end opposite of and spaced from the mounting portion, the free end being disposed in relation to a vacuum port at a predetermined second location in the chamber and bounded by a seat, the free end of the tongue being sufficiently resiliently flexible so as to be bendable at locations spaced from the mounting portion into a curved shape in a range of modulated positions proportionally spaced from the seat responsive to the vacuum flow when greater than the low vacuum flow conditions to allow the vacuum flow between the free end and the seat, and the free end of the tongue having an unmodulated closed position responsive to the low vacuum flow conditions disposed against the seat in covering relation to the vacuum port to seal the vacuum port except for a small vacuum orifice in a surface of the tongue facing the seat or in the seat and extending from a side of the tongue to the vacuum port between the free end and a portion of the tongue extending from the middle of the vacuum port to the mounting portion, the vacuum orifice having a cross sectional flow area substantially smaller than a cross sectional flow area of the vacuum port sufficient to communicate an amount of vacuum flow through the orifice substantially smaller than an amount of vacuum flow through the vacuum port when the free end is in the modulated positions, and the free end having a resilient property that combined with the small size of the orifice damps and limits transmission of high amplitude oscillations in the communicated vacuum pressure when the free end is unmodulated and substantially unmodulated, the free end of the tongue when bent at the locations spaced from the mounting portion into the curved shape in the range of modulated positions proportionally spaced from the seat, extends toward the predetermined first location in the chamber and with the seat bounds a wedge shape entrance region that faces toward the nozzle of the vacuum source or the vacuum generator port communicating with the vacuum source and extends convergingly toward the vacuum port, such that the resilient property of the free end will absorb and damp a portion of any high amplitude pressure oscillations that enter the wedge shape entrance region and the free end is positioned to deflect pressure spikes away from the vacuum port and into the chamber, and wherein the vacuum orifice comprises at least one groove in the surface of the flexible tongue, and the groove extends completely across the surface of the flexible tongue and connects to openings on opposite sides thereof.

2. The vacuum system of claim 1, wherein the seat comprises a generally flat surface and the free end of the tongue of the damper is flat when unmodulated so as to rest against the flat surface.

3. The vacuum system of claim 1, wherein the flexible tongue comprises a material configured to at least partially absorb the oscillations in the vacuum pressure, and to enable the free end of the flexible tongue to flex or bend at the location spaced from the mounting portion in a manner of a tongue to modulate responsive to the vacuum flow.

4. The vacuum system of claim 1, wherein the vacuum source comprises a vacuum generator including the nozzle, configured to produce the vacuum pressure and the vacuum flow by flow of pressurized air or gas therethrough.

5. The vacuum system of claim 4, wherein the vacuum generator is configured to produce the vacuum pressure in at least a range of between about −550 mm Hg and about −700 mm Hg. during the low vacuum flow conditions.

6. The vacuum system of claim 4, wherein the vacuum generator is contained in the housing.

7. The vacuum system of claim 6, wherein the housing includes
a unitary element including a passage containing the vacuum generator; and
a retaining element for receiving the mounting portion of the flow-modulated damper, including a protrusion that is received in a receptacle in the mounting portion of the damper.

8. A vacuum system, comprising:
a vacuum source configured and operable to generate vacuum pressure;
a vacuum using device or system;
an enclosed vacuum flow path connecting the vacuum source to the vacuum using device or system, for communicating the vacuum pressure thereto and vacuum flow therefrom; and
a minimally flow restrictive flow-modulated vacuum pressure oscillation reducing damper disposed in the vacuum flow path between the vacuum source and the vacuum using device or system, the damper having a restrained mounting portion and a resiliently flexible element extending therefrom configured to be modulated into a resiliently curved shape in a range of acute angular relations to a surface about a vacuum port of the flow path responsive to the vacuum flow conditions when above about 1 cubic foot per minute so as to resiliently flex away from the surface about the vacuum port in a manner of a tongue to open the vacuum port and present a wedge shaped entrance region between the vacuum source and the port facing the vacuum source, the wedge shaped entrance region having a size proportional to an amount of the flow and being bounded by the surface about the vacuum port and the flexible element in the resiliently curved shaped so as to damp oscillations in the vacuum flow communicated to the vacuum using device or system and to deflect pressure spikes away from the vacuum orifice, the flexible element being substantially unmodulated to close against the surface responsive to low vacuum flow conditions of less than about 1 cubic foot per minute at vacuum greater than about −550 mm Hg., the resiliently flexible element having a surface facing the surface about the vacuum port, including at least one vacuum orifice spaced from the mounting portion and extending to about a middle of the vacuum port to define a free end portion of the resiliently flexible element extending to a distal end thereof, the vacuum orifice being substantially smaller than the vacuum port and configured to communicate the low vacuum flow conditions from the using device or system when the flexible element is unmodulated, the resilience of the damper in combination with the small size of the vacuum orifice being further configured to damp oscillations in the vacuum pressure communicated therethrough to the vacuum using device or system during the low vacuum flow conditions, and the resiliently flexible element having a partially modulated position wherein only the free end portion has a curved shape bounding the wedge shaped entrance region facing the vacuum source and a portion of the resiliently flexible element extending from the at least one vacuum orifice to the mounting portion has a flat shape and abuts the surface of the vacuum port, and wherein the at least one vacuum orifice comprises at least one groove in the surface of the flexible element that extends completely across the surface of the flexible element and connects to openings on opposite sides thereof and increases flexibility of the flexible element at the groove.

9. The vacuum system of claim 8, wherein the free end portion is configured when the flexible element is unmodulated to lay against the surface about the vacuum port to substantially close the vacuum port except the at least one vacuum orifice, and when the flexible element is modulated, to flex away in the curved shape from the surface about the vacuum port.

10. The vacuum system of claim 8, wherein the flexible element comprises a material configured to at least partially absorb the oscillations in the vacuum pressure, and to enable the free end portion of the resiliently flexible element extending from the at least one vacuum orifice to the mounting portion to flex or bend in a curve spaced from the mounting portion when fully modulated responsive to the vacuum flow.

11. The vacuum system of claim 8, wherein the at least one vacuum orifice has a cross sectional flow area substantially smaller than a cross sectional flow area of the vacuum port and faces laterally relative to the vacuum source, the at least one vacuum orifice being configured to communicate an amount of vacuum flow through the orifice when the damper is unmodulated which is substantially smaller than an amount of the vacuum flow through the vacuum port when the damper is at least partially modulated.

12. A vacuum system, comprising:
a vacuum source configured and operable to generate vacuum pressure;
an enclosed vacuum flow path for connecting the vacuum source to a vacuum using device or system for communicating the vacuum pressure thereto and vacuum flow therefrom; and
a minimally flow restrictive flow-modulated vacuum pressure oscillation reducing damper disposed in the vacuum flow path, configured to communicate the vacuum pressures to the vacuum using device or system and to allow the vacuum flow therefrom under all conditions, configured to be modulated responsive to the vacuum flow and flexible so as to open the path proportionally to an amount of the flow over a full range of the generated vacuum pressures, and to be at least substantially unmodulated responsive to low vacuum flow conditions, the damper comprising a restrained mounting portion and a resiliently flexible tongue extending in one direction from the mounting portion and having a free end opposite of and spaced from the mounting portion, the free end being disposed in relation to a vacuum port bounded by a seat and sufficiently flexible to have a range of modulated positions proportionally spaced from the seat responsive to the vacuum flow to allow the vacuum flow between the free end and the seat, and having an unmodulated closed position responsive to low vacuum flow conditions disposed against the seat in covering relation to the vacuum port to seal the vacuum port except for a small vacuum orifice comprising at least one groove in a surface of the tongue facing the seat and extending completely across the surface of the flexible tongue and a middle of the vacuum port to connect to openings on opposite sides of the tongue between the free end and a portion of the tongue extending from the middle of the vacuum port to the mounting portion, the vacuum orifice having a cross sectional flow area substantially smaller than a cross sectional flow area of the vacuum port sufficient to communicate an amount of vacuum flow through the orifice substantially smaller than an amount of vacuum flow through the vacuum port when the free end is in the modulated positions, and the free end having a resilient property that combined with the small size of the orifice damps and limits transmission of high amplitude oscillations in the communicated vacuum pressure when the free end is unmodulated and substantially unmodulated and that enables the free end to have a partially modulated position resiliently flexed in a curved shape away from the seat while the portion of the tongue extending from the middle of the vacuum port to the mounting portion is disposed against the seat.

13. A vacuum system, comprising:
a vacuum source configured and operable to generate vacuum pressure;
a vacuum using device or system;
an enclosed vacuum flow path connecting the vacuum source to the vacuum using device or system, for communicating the vacuum pressure thereto and vacuum flow therefrom; and
a minimally flow restrictive flow-modulated vacuum pressure oscillation reducing damper disposed in the vacuum flow path, the damper having a restrained mounting portion and a resiliently flexible element extending therefrom configured to be modulated relation to a surface about a vacuum port of the flow path responsive to the vacuum flow conditions when above about 1 cubic foot per minute so as to resiliently flex away from the surface about the vacuum port in a manner of a tongue to open the vacuum port and present a wedge shaped entrance region between the vacuum source and the port facing the vacuum source, the wedge shaped entrance region having a size proportional to an amount of the flow and being bounded by the surface about the vacuum port and the flexible element so as to damp oscillations in the vacuum flow communicated to the vacuum using device or system, the flexible element being substantially unmodulated to close against the surface responsive to low vacuum flow conditions of less than about 1 cubic foot per minute at vacuum greater than about −550 mm Hg., the resiliently flexible element having a surface facing the surface about the vacuum port, including at least one vacuum orifice spaced from the mounting portion and comprising at least one groove in a surface of the flexible element facing the seat, the at least one groove extending completely across the surface of the flexible element and a middle of the vacuum port to connect to openings on opposite sides of the flexible element to increase flexibility thereof at the groove and define a free end portion of the flexible element extending to a distal end thereof, the at least one vacuum orifice being substantially smaller than the vacuum port and configured to communicate the low vacuum flow conditions from the using device or system when the flexible element is unmodulated, the resilience of the damper in combination with the small size of the vacuum orifice being further configured to damp oscillations in the vacuum pressure communicated to the vacuum using device or system during the low vacuum flow conditions, and the flexible element having a partially modulated position wherein the free end portion has a curved shape bounding the wedge shaped entrance region and a portion of the flexible element extending from the at least one vacuum orifice to the mounting portion has a flat shape and abuts the surface of the vacuum port.

* * * * *